United States Patent
Lin et al.

(10) Patent No.: US 9,459,247 B2
(45) Date of Patent: Oct. 4, 2016

(54) QUANTITATIVE MEASUREMENT OF NANO/MICRO PARTICLE ENDOCYTOSIS WITH CELL MASS SPECTROMETRY

(75) Inventors: Huan-Chang Lin, Taipei (TW); Hsin-Hung Lin, Taipei (TW); Cai-Yu Kao, Taipei (TW); Alice L Yu, La Jolla, CA (US); Wen-Ping Peng, Taipei (TW); Chung-Hsuan Chen, Taipei (TW)

(73) Assignee: Academia Sinica, Taipei (TW)

( * ) Notice: Subject to any disclaimer, the term of this patent is extended or adjusted under 35 U.S.C. 154(b) by 611 days.

(21) Appl. No.: 13/075,160

(22) Filed: Mar. 29, 2011

(65) Prior Publication Data

US 2011/0236882 A1  Sep. 29, 2011

Related U.S. Application Data

(60) Provisional application No. 61/318,391, filed on Mar. 29, 2010.

(51) Int. Cl.
| | |
|---|---|
| *A61K 45/06* | (2006.01) |
| *C12Q 1/70* | (2006.01) |
| *G01N 33/50* | (2006.01) |
| *G01N 33/569* | (2006.01) |
| *G01N 33/68* | (2006.01) |

(52) U.S. Cl.
CPC ...... *G01N 33/5091* (2013.01); *G01N 33/5008* (2013.01); *G01N 33/569* (2013.01); *G01N 33/6848* (2013.01)

(58) Field of Classification Search
CPC .............................. C08L 71/02; A61K 31/337
See application file for complete search history.

(56) References Cited

U.S. PATENT DOCUMENTS 8,206,747 B2 * 6/2012 Zale et al. ............... 424/489

FOREIGN PATENT DOCUMENTS

WO    WO 2009/076535    *  6/2009    ............... G01J 3/40

OTHER PUBLICATIONS

Peng et al. (Anal. Chem. 2008, 80, pp. 2524-2530).*
Zhu et al. (JACS, 2008, 130, p. 14143-14139).*
Jain et al. (Molecular Pharmaceutics, 2005, pp. 194-205).*
Lin et al. Cell Mass Spectrometry, Apr. 13, 2010, 3460-3464.*

* cited by examiner

*Primary Examiner* — Agnieszka Boesen
(74) *Attorney, Agent, or Firm* — Eckman Basu LLP

(57) ABSTRACT

Methods for detecting the presence of nanoparticles or microparticles by cell mass spectrometry (CMS) are provided. CMS methods are provided for determining the number of nanoparticles or microparticles in each cell. Nanoparticles whose intracellular concentration can be determines by the CMS methods of the invention include polymeric nanoparticles (NPs), liposomes, viral-based NPs, carbon nanotubes, diamond NPs, polymeric micelles, nanocarriers, liposomes, and viral nanoparticles. Determination of the efficiency of drug delivery and intracellular titer of pathogens according to the invention is disclosed. Methods for determining intracellular uptake of virus particles are provided.

20 Claims, 7 Drawing Sheets

Fig. 4
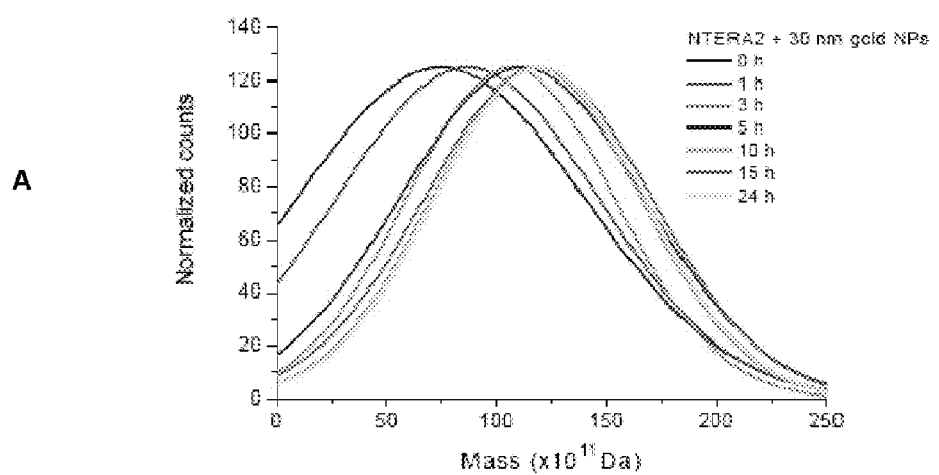
A
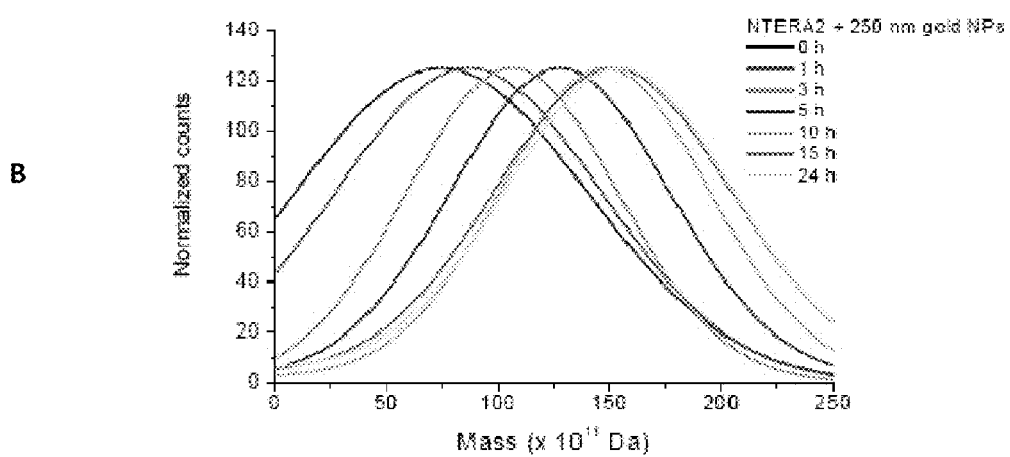
B

Fig. 5
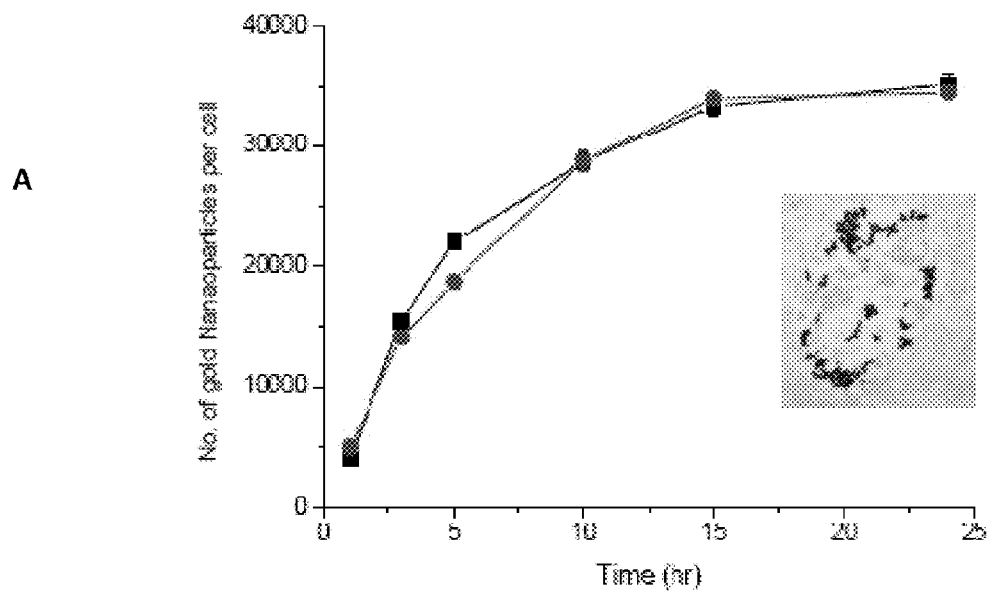
A
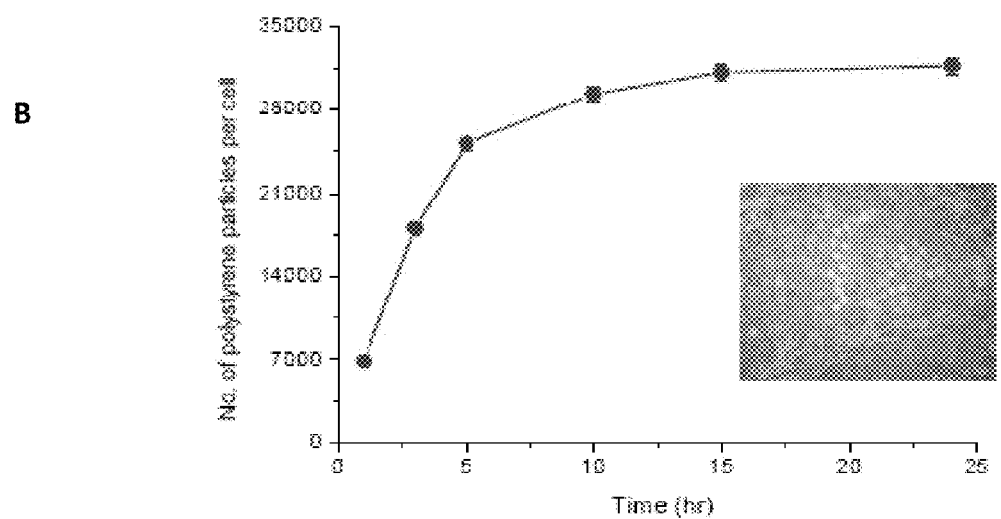
B

QUANTITATIVE MEASUREMENT OF NANO/MICRO PARTICLE ENDOCYTOSIS WITH CELL MASS SPECTROMETRY

CROSS-REFERENCE TO RELATED PUBLICATIONS

This patent application claims the benefit of U.S. Provisional Patent Application Ser. No. 61/318,391, filed Mar. 29, 2010, entitled "Quantitative Measurement of Nano/Micro Particle Endocytosis with Cell Mass Spectrometry" the contents of which are incorporated herein in their entirety by reference.

TECHNICAL FIELD OF THE INVENTION

The present invention relates to cell mass spectrometry. Specifically, the invention relates to detecting the presence of nanoparticles or microparticles inside a cell by mass spectroscopy. More specifically, the invention relates to determining the number of nanoparticles or microparticles inside a cell by mass spectroscopy.

BACKGROUND OF THE INVENTION

Nano/microparticles have been actively pursued as an efficient way for drug delivery. Therefore, quantitative measurement of cellular uptake of nano/micro particles is of great importance in understanding the mechanisms of cell endocytosis and exocytosis process. (B. D. Chithrani, A et al., *Nano Lett.* 2006, 6, 662; B. D. Chithrani, W. C. W. Chan, *Nano Lett.* 2007, 6, 1542; F. Osaki, et al., *J. Am. Chem. Soc.* 2004, 126, 6520; J. A. Champion, S. Mitragotri, *Proc. Natl. Acad. Sci. U.S.A.* 2006, 103, 4930; H. Jin, et al., *ACS nano* 2009, 3, 149.)

The conventional ways for quantifying nano/micro particle uptake into mammalian cells involve both inductively coupled plasma atomic emission spectroscopy (ICP-AES; B. D. Chithrani, et al., *Nano Lett.* 2006, 6, 662; B. D. Chithrani, W. C. W. Chan, *Nano Lett.* 2007, 6, 1542; F. Osaki, et al., *J. Am. Chem. Soc.* 2004, 126, 6520; J. A. Champion, S. Mitragotri, *Proc. Natl. Acad. Sci. U.S.A.* 2006, 103, 4930; H. Jin, et al., *ACS nano* 2009, 3, 149; J. A. Ryan, et al., *Anal. Chem.* 2007, 79, 9150) and inductively coupled plasma mass spectrometry (ICP-MS; P. Yang, et al., *Bioconjugate Chem.* 2005, 16, 494). These are accurate but are limited to elemental species, such as gold nanoparticles (NPs). Recently, laser desorption/ionization mass spectrometry has been employed to achieve quantitative measurements of gold NPs uptake by cells with the gold NPs encoded with different functional groups as mass barcodes. (Z.-J. Zhu, et al., *J. Am. Chem. Soc.* 2008, 130, 14139) However, the encoding process is tedious and time consuming.

There is a need to provide a rapid means for quantifying nano/micro particle uptake into mammalian cells. There is a need for a means for quantifying uptake into mammalian cells of all types of nanoparticles including non-metallic nano/micro particles such as polymeric nanoparticles (NPs), liposomes, viral-based NPs, carbon nanotubes, diamond NPs, and polymeric micelles. Further, there is a need for a means for quantifying uptake into mammalian cells of all types of pathogenic nanoparticles including, but not limited to, viruses, bacteria, prions, yeast, fungi, and parasites.

SUMMARY OF THE INVENTION

This invention provides a novel approach to investigate and determine the amounts of pathogenic and non-pathogenic nano/micro particle uptake into mammalian cells.

Cell mass spectrometry (CMS) is a rapid and accurate method for determining the quantity of gold NP uptake into cells. It can determine the number of NP uptake on each individual cell whereas ICP only get a mean of all cells. In addition, it can be used to measure not only the cellular uptake of metal nanoparticles but also the non-metal nano/micro particles. In some embodiments, the cell mass spectrometry is charge monitoring cell mass spectrometry (CM-CMS).

The invention relates to a method for determining uptake of nanoparticles or microparticles by a cell, the method comprising the steps of: (a) providing a cell contacted with a nanoparticle or microparticle of known dimension under conditions suitable for uptake of the nanoparticle or microparticle by the cell; (b) recording a mass spectrum of the cell by cell mass spectrometry in the presence and absence of exposure to the nanoparticle or microparticle; and (c) determining a shift in mass/charge (m/z) ratio, wherein a shift in the m/z ratio corresponds to an uptake of the nanoparticle or microparticle by the cell. The method further comprises: converting acquired values of m/z and the corresponding charge (z) on each cell to an absolute mass of measured cells.

The invention relates to a method for quantifying a number of nanoparticles or microparticles taken up by a cell, the method comprising the steps of: (a) providing a cell suspected of being contacted with a nanoparticle or microparticle of known dimension under conditions suitable for uptake of the nanoparticle or microparticle by the cell; (b) recording a mass spectrum of the cell by cell mass spectrometry; (c) converting acquired values of m/z and the corresponding charge (z) on each cell to a mass of the cell; (d) determining a mean mass difference; and (e) comparing the mean mass difference to a predetermined difference corresponding to a known number of the nanoparticle or microparticle of known dimension.

The methods may further comprise taking measurements over time; and determining a time-resolved uptake profile of the nanoparticle or microparticle by the cell.

In one aspect the invention provides a method for measuring drug uptake by a target cell, the method comprising: contacting a target cell with a drug nanoparticle; and determining the number of drug nanoparticles taken up by the target cell by a method according to the invention. The drug is selected from the group consisting of antibiotics, non-steroidal (NSAIDs) and steroidal anti-inflammatory agents, anti-histamines, mast cell stabilizers, anti-allergy agents, and anti-cancer agents.

In one aspect the invention provides a method for measuring the titer of a pathogen inside an infected cell, the method comprising: providing a cell infected with a suspected pathogen nanoparticle or microparticle; and determining the number of pathogen nanoparticles or microparticles within the infected cell by a method according to the invention, wherein the mass spectrum information of the infected cell is compared to that of an infected cell of the same type. In some embodiments, the pathogen is selected from a virus, a bacteria, a prion, an yeast, a fungus, and a parasite. In some embodiments, the infected call is a human cell.

In one aspect, the pathogen is a virus particle. Thus, the invention provides methods for measuring intracellular uptake of a virus particle by a virus-infected mammalian cell, wherein the virus is selected from the group consisting of Influenza, Measles, Coronavirus, Mumps, Marburg, Ebola, Rubella, Rhinovirus, Poliovirus, Hepatitis A, Smallpox, Chicken-pox, Severe Acute Respiratory Syndrome virus or SARS virus.

The nanoparticle or microparticle has a dimension less than or about 10 µm, less than or about 5 µm, less than or about 3 µm, less than or about 1 µm, less than or about 500 nm, less than or about 250 nm, less than or about 100 nm, less than or about 50 nm, less than or about 30 nm, less than or about 20 nm, less than or about 10 nm, or less than or about 5 nm.

The nanoparticle or microparticle can be metallic, for example, gold, silver, palladium or any suitable metal.

In some embodiments, the nanoparticle or microparticle is non-metallic comprising polystyrene, polymeric nanoparticles (NPs), liposomes, viral-based NPs, carbon nanotubes, diamond NPs, and polymeric micelles, a nanocarrier, a liposome, a drug nanoparticle, or viral nanoparticles.

In some embodiments, the nanoparticle is a lipidic particle is selected from a liposome, a lipid-nucleic acid complex, a lipid-drug complex, a solid lipid particle, and a microemulsion droplet.

In some embodiments, the nanoparticle comprises a suitable biomolecule attached to a nanocarrier particle, wherein the biomolecule is selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof.

In some embodiments, the nanoparticle further comprises an incorporated bioactive moiety selected from the group consisting of diagnostic agents, contrast agents, radionuclides, fluorescent, luminescent, and magnetic moieties, prophylactic agents, vaccines, and nutraceutical agents.

In some embodiments, the nanoparticle further comprises an incorporated therapeutic agent selected from the group consisting of small molecules, nucleic acids, siRNA, RNAi, microRNA, proteins, antibodies, peptides, lipids, carbohydrates, hormones, metals, radioactive compounds, drugs, vaccines, immunological agents and combinations thereof.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 4a-4b shows cellular uptake kinetics of (4a) 30 nm and (4b) 250 nm gold nanoparticles respectively.

FIG. 5a-5b shows cellular uptake kinetics of (5a) 50 nm gold nanoparticles by NTERA2 cells as a function of incubation time by CMS (red circle) and ICP-MS (black squares) techniques, and of (5b) 100 nm polystyrene particles by Raw264.7 cells as a function of incubation time, respectively. (Inserted photos are TEM images).

DETAILED DESCRIPTION OF THE INVENTION

Figure 1:
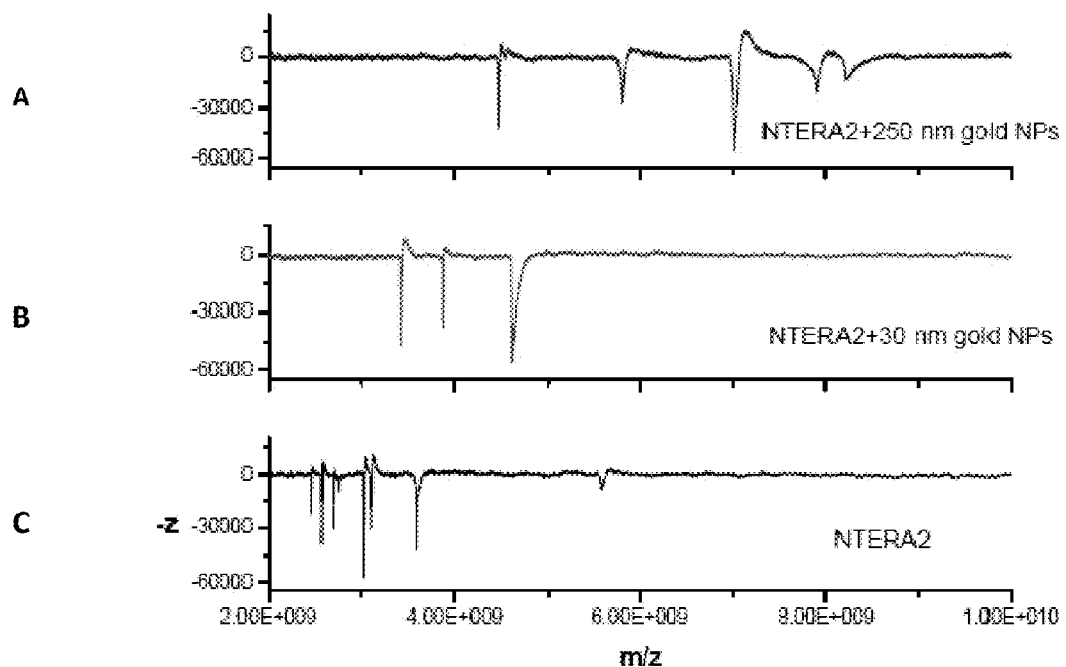
FIG. 1a-1b shows mass spectra of NTERA2 cells after uptake of (FIG. 1a) 250 nm gold nanoparticles and (FIG. 1b) 30 nm gold nanoparticles.
FIG. 1c shows mass spectrum of NTERA2 cell.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The process by which cells absorb particles (such as proteins) from outside the cell by engulfing it with their cell membrane is known as endocytosis. Endocytosis regulates many processes, including nutrient uptake, pathogen entry, antigen presentation, and drug delivery. Among various endocytic pathways, clathrin-mediated endocytosis involves small (approx. 100 nm in diameter) vesicles that have a morphologically characteristic crystalline coat made up of a complex of proteins mainly associated with the protein clathrin. Clathrin-coated vesicles (CCVs) are found in virtually all cells and form domains of the plasma membrane termed clathrin-coated pits.

Uptake of extracellular molecules is also believed to be specifically mediated via receptors in caveolae which consist of the cholesterol-binding protein caveolin (Vip21) with a bilayer enriched in cholesterol and glycolipids. Caveolae are small (approx. 50 nm in diameter) flask-shape pits in the membrane. Macropinocytosis is the invagination of the cell membrane to form a pocket, which then pinches off into the cell to form a vesicle (0.5-5 nm in diameter) non-specifically filled with large volume of extracellular fluid and molecules. Phagocytosis is the process by which cells bind and internalize particulate matter larger than around 0.75 nm in diameter, such as small-sized dust particles, cell debris, micro-organisms and even apoptotic cells.

Ligand-receptor pairs, viruses and other pathogens, as well as non-viral gene delivery vectors are known to enter cells by receptor binding followed by cell entry via receptor-mediated endocytosis into clathrin-coated pits and vesicles. Certain toxins and pathogens, such as anthrax toxin, harness clathrin-mediated internalization to enter cells. Clathrin-mediated pathway appears to be exploited not only by viruses, but also by much larger bacterial pathogens such as *Listeria monocytogenes*. Prions and some bacteria enter cells by other clathrin-independent routes. (See Miaczynska M. et al., J. Cell Biol. 2008 Jan. 14; 180(1): 7.11).

Nanoparticles have important biomedical applications ranging from the treatment of human disease with gene therapy to understanding basic cellular functions with labeled probes. It is now possible to synthesize nanoparticles with nearly any property or size, direct them to specific cells, and functionalize them to target intracellular locations.

However, efficient and accurate methods for measuring the uptake of the nanoparticles are lacking.

Cell mass spectrometry (CMS) has been developed to directly measure the masses of cells in gas phase. Rapid determination of mass distribution of cells and polystyrene microparticles has been demonstrated by measuring both mass-to-charge ratio (m/z) and charge (z) simultaneously. (W.-P. Peng, et al. *Angew. Chem. Int. Ed.* 2007, 46:3865; W-P. Peng, et al. *Anal. Chem.* 2008, 80, 2524). Mass spectra over the range of m/z values from 109 to 1012 were obtained with good signal-to-noise ratios. Different types of mononuclear cells, cancer cells, and red blood cells were clearly distinguished. (W.-P. Peng, et al. *Angew. Chem. Int. Ed.* 2007, 46, 3865; Z. Nie, et al. *Anal. Chem.* 2007, 79, 7401; Z. Nie, et al., *Int. J. Mass Spectrom.* 2008, 270, 8). By these methods, mass resolutions of ~100 and mass accuracies of ~1% were achieved. (Z. Nie, et al., *Int. J. Mass Spectrom.* 2008, 270:8). Results measured by CMS were about the same as that by ICPMS. A CMS can be based on either light scattering or charge measuring (CMCMS) to measure the mass of a selected cell.

Methods for detecting nanoparticles using the cell mass spectrometer are disclosed in PCT Application Pub. No. WO/2009/076535, which is incorporated herein in its entirety by reference. WO/2009/076535 discloses an apparatus including components for mounting and desorbing/vaporizing the analyte; components for enhancing the electrostatic charge of the analyte; a mass analyzer for determining the mass to charge (m/z) ratio of the analyte based on its interactions with an electric and/or magnetic field; and a charge detector to measure the charge of the analyte. The methods disclosed in WO/2009/076535 can be used for direct detection of bioparticles (such as viruses, macromolecular complexes, ribosomes, organelles, mitochondria, chloroplasts, synaptosomes, chromosomes, whole cells, cancerous cells, bacterial cells, pollen grains, and spores. The methods disclosed in WO/2009/076535 also are suitable for direct measurement of small molecules, nanoparticles, microparticles, and polymers.

Cellular Uptake of Microparticles and Nanoparticles

It has been surprisingly found that mass spectrometric methods can be used to detect and measure the uptake of particles by cells. The kind of particle can be nanoparticles, microparticles, virus, proteins and small molecule drugs. The present invention measures the mass difference of cell to determine the number of particles taken up by a cell. In one embodiment, the number of nanoparticles taken by the cell is measured.

Charge monitoring cell mass spectrometry (CMCMS) has been developed for rapid measurement of mass and mass distribution of cells and microparticles. Controlled discharge can enhance the number of charges on a microparticle to increase the accuracy of mass measurement by CMCMS. (W.-P. Peng, et al. *Anal. Chem.* 2008, 80, 2524).

The masses of intact bioparticles, including viruses, bacteria, and whole mammalian cells have indeed been measured with mass spectrometers employing soft desorption techniques, such as laser-induced acoustic desorption (LIAD). Mass spectrometric analysis generally requires that the analyte be vaporized into the gas phase for subsequent analysis, particularly by the mass analyzer. Desorption is a commonly used process to vaporize analyte into the gas phase. Multiple types of desorption may be used in accordance with the invention. Laser-Induced Acoustic Desorption (LIAD) may be used by configuring the apparatus with a substrate on which the analyte may be mounted, without an underlying matrix. Laser irradiation of the substrate may be used to desorb the analyte from the substrate, such that the analyte enters the gas phase and is subject to the electric and/or magnetic fields generated by other components of the apparatus.

Other versions of desorption include, without limitation, Matrix-Assisted Laser Desorption Ionization (MALDI), Surface-Enhanced Laser Desorption Ionization (SELDI), Desorption-Ionization On Silicon (DIOS), Desorption Electrospray Ionization (DESI), Plasma Desorption, and Field Desorption (FD). Additional modes of desorption are also included within this invention, such as Electron Ionization (EI), Chemical Ionization (CI), Field Ionization (FI), Fast Atom Bombardment (FAB), Ion Attachment Ionization (IA), Electrospray (ES), Thermospray (TS), Atmospheric Pressure Ionization (API), Atmospheric Pressure Photoionization (APP), Atmospheric Pressure Chemical Ionization (APCI), and Direct Analysis in Real Time (DART).

A mass analyzer employing a trap may be used for light-scattering measurements to determine the mass-to-charge ratio (m/z) for these desorbed bioparticles. The mass analyzer may use an electromagnetic field to sort analytes in space or time according to their mass to charge ratio. The invention may relate to mass spectrometers employing many types of mass analyzer. The analyte may be analyzed in an ion trap. The ion trap may be a three-dimensional quadrupole ion trap, also known as a Paul Ion Trap, which may have end cap electrodes and a ring electrode. The end cap electrodes may be hyperbolic. The end cap electrodes may be ellipsoid. Holes may be drilled in the end cap electrodes to allow observation of light scattering and through which analyte may be ejected. The frequency of oscillation may be scanned to eject analyte from the trap according to its mass to charge ratio. The ion trap may be a linear ion trap (LIT), also known as a two dimensional ion trap. The LIT may be coupled with more than one detector so as to detect analyte ejected axially and radially.

The mass analyzer may be a time-of-flight analyzer. The time of flight analyzer may include electrodes to generate an electric field in one region to accelerate the analyte, followed by a field-free region, followed by a detector. The time of flight analyzer may be a reflectron time of flight analyzer, in which a reflectron or electrostatic reflector may increase the total flight length and time of the analyte. The time of flight analyzer may operate by delayed pulse extraction, in which the accelerating field is controlled in a manner to correct ion energy dispersion and/or is present only after a delay following absorption. The time of flight analyzer may operate by continuous extraction, in which the accelerating field is continuously present in its region during analysis. Additional mass analyzers that may be adapted for use with the invention include, without limitation, quadrupole, magnetic sector, orbitrap, and ion cyclotron resonance analyzers.

The charge monitoring cell mass spectrometer (CMCMS) is able to measure the masses of cells/microparticles with high speed. For this device, cell or microparticle samples are deposited onto a Si wafer. Laser-induced acoustic desorption (LIAD) is used to desorb cells/microparticles into the ion trap. The m/z ratios of the cells are determined by scanning the trapping frequency to eject charged cells. A Faraday disc is used to measure the number of charges (z) on the particle so that the mass of the charged particle can be determined There are a few specific features for CMCMS compared to most conventional commercial mass spectrometers. They include (1) LIAD to desorb charged particles into the quadrupole ion trap (QIT), (2) a very high m/z ratio obtained using a frequency scan which operates in mass-selective instability mode, (3) direct measurement of the number of charges (z) on a particle without secondary electron amplification, and (4) a corona discharge to enhance the number of charges onto a microparticle. (Id.)

To verify that CMS instrument is able to quantify the cellular uptake of nano/micro particles, NTERA2 cells were first incubated with 30 nm and 250 nm gold nanoparticles (NPs) and their mass spectra were recorded. The m/z range of the mass spectra ranged from 109 to 1010. The charges carried on each cell, typically larger than ten thousand, were detected by the Faraday plate charge detector. FIG. 1 shows that the observed mass peaks of NTERA2 cells with gold NP uptake are shifted to higher m/z range.

Figure 2:
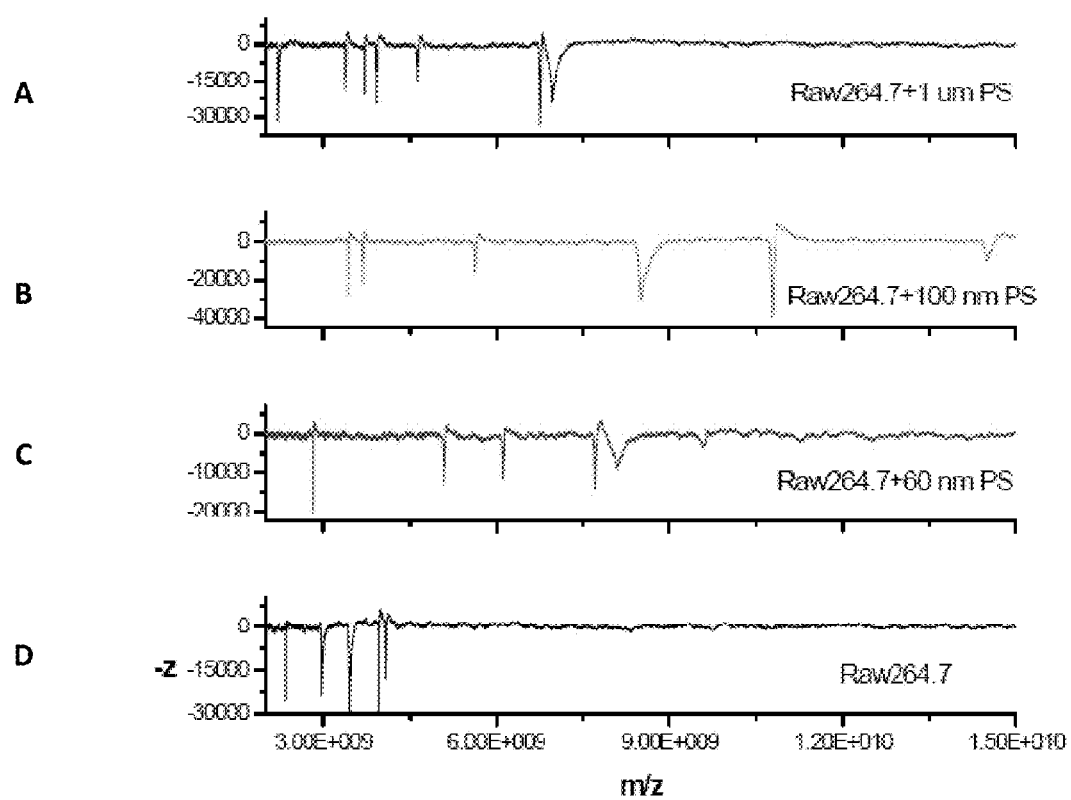
FIG. 2a-2c shows mass spectra of Raw264.7 cells after uptake of (2a) NIST 1 µm polystyrene particles, (2b) NIST 100 nm polystyrene particles and (2c) NIST 60 nm polystyrene particles.
FIG. 2d shows mass spectrum of Raw264.7 cell.

As shown in FIG. 2, similar experimental results were obtained when Raw264.7 cells took up 60 nm, 100 nm and 1 μm NIST polystyrene (non-metallic) particles. All the polystyrene size standard particles used in this paper were purchased from National Institute of Standards and Technology (NIST). The Standard Reference Material (SRM) samples included SRM 1964 (60 nm), SRM 1963 (0.1 μm), SRM 1691 (0.3 μm), and SRM 1690 (1 μm). The observed mass peaks were in the range of 109 to 1010.

Figure 3:
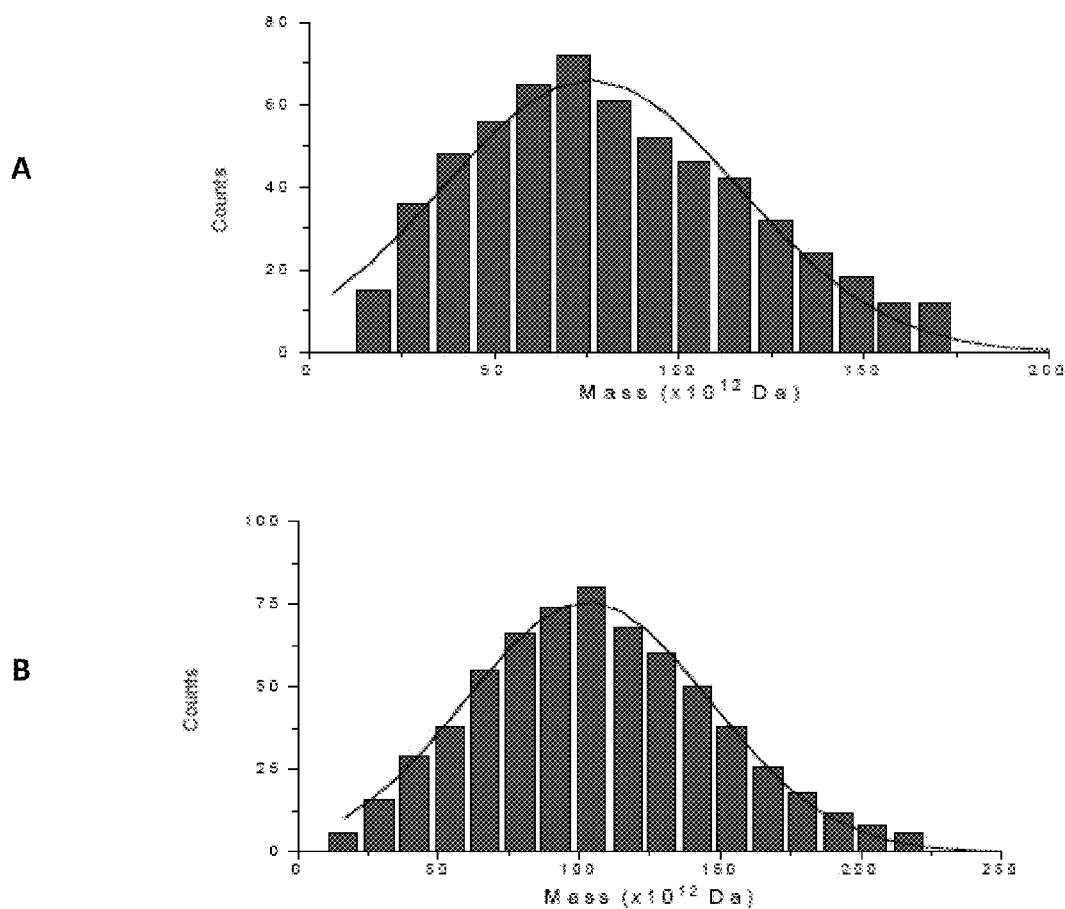
FIG. 3a-3b shows mass histogram analysis of (3a) NTERA2 cells and (3b) NTERA2 cells with 30 nm gold nanoparticles uptake, respectively.
Figure 6:
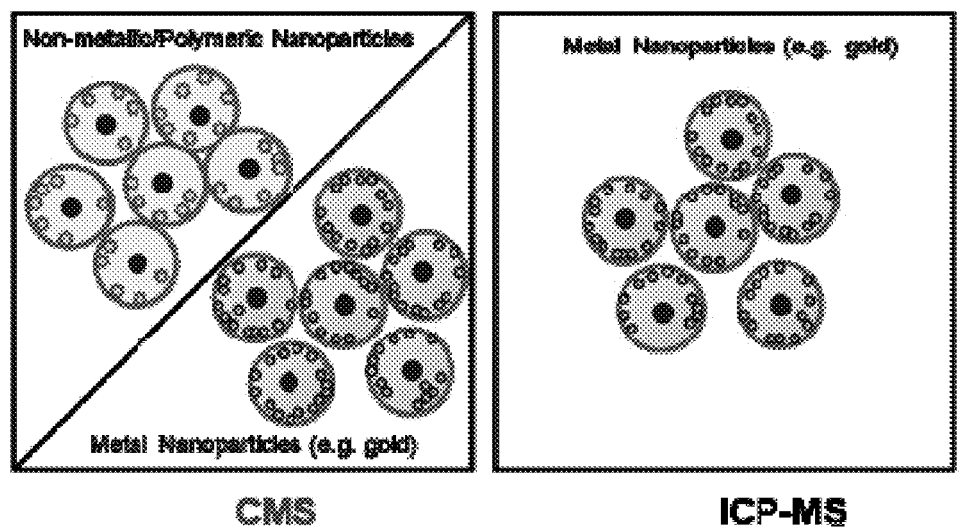
FIG. 6 shows determination of the quantity of nano/micro particles taken up into cells using cell mass spectrometry (CMS). The uptake amounts of gold nanoparticle as determined by cell mass spectrometry was about the same as that by inductively coupled plasma mass spectrometry (ICP-MS).

Typical mass histogram analysis of NTERA2 uptake of gold NP and without gold NP are shown in FIG. 3b and FIG. 3a, respectively. For each mass histogram analysis, more than six hundred cells were measured by CMS. The acquired values of m/z and the corresponding charge (z) on each cell were converted to the absolute mass of measured cells. It was noted the truncation of high mass clusters was essential while performing the Gaussian fitting procedure. Mass histogram analysis of the collected mass spectra of 3 μm NIST polystyrene particles showed that the mean mass deviated about 1.8% after repeating eight measurements. Mass accuracy of ~2.1% was obtained while HeLa cells were with gold NP uptake. The mass accuracy of this CMS instrument was able to distinguish between cells with and without the uptake of gold NPs.

The cellular uptakes of gold NPs as a function of incubation time for sizes of 30 nm and 250 nm are shown in the FIG. 4. The difference in the mean mass was measured about 60% after incubation for 24 h for 30 nm gold NPs taken up by NTERA2 cells. This mean mass difference corresponds to ~260,000 of 30 nm gold NPs as shown in FIG. 4a. FIG. 4b shows a mean mass deviation of 200% which corresponds to uptake of ~800 gold NPs of 250 nm size by the NTERA2 cells after 24 h of incubation.

Shown in FIG. 5a is the uptake kinetics of 50 nm gold NPs into NTERA2 cells using both CMS and ICP-MS. The uptake trend and amount of both measurements was similar. For the CMS measurements, the cell weights were determined after the cells were fixed with 4% paraformaldehyde in PBS.

Therefore, CMS measures each individual cell and thus reflects the uptake amounts of gold NP by cells. From these results, it indicates cell mass spectrometry is an adequate tool for time-resolved measurements of nanogold uptake by cells. The cellular uptake kinetics of polystyrene nanoparticles using Raw264.7 cell line was measured as shown in FIG. 5b.

CMS not only is a rapid and accurate method for determining the quantity of gold NP uptake into cells, it can determine the number of NPs taken up by each individual cell whereas ICP only get a mean of all cells.

Together with the quantitative measurement of gold NPs, CMS is a valuable tool for its applications in quantifying all types of nanoparticles (K. Cho, et al., *Clin Cancer Res.*, 2008, 14, 1310) including polymeric nanoparticles (NPs: B. L. Zhang, et al., *Small,* 2009, 5, 2716), liposomes, viral-based NPs, carbon nanotubes, diamond NPs (H. J. Johnston, et al., *Toxicol. Appl. Pharmacol.* 2010, 242, 66), and polymeric micelles.

In certain embodiments, the microparticles or nanoparticles are lipidic particles. Lipidic particles are microparticles or nanoparticles that include at least one lipid component forming a condensed lipid phase. Typically, a lipidic nanoparticle has preponderance of lipids in its composition. The exemplary condensed lipid phases are solid amorphous or true crystalline phases; isomorphic liquid phases (droplets); and various hydrated mesomorphic oriented lipid phases such as liquid crystalline and pseudocrystalline bilayer phases (L-alpha, L-beta, P-beta, Lc), interdigitated bilayer phases, and nonlamellar phases (inverted hexagonal H-I, H-II, cubic Pn3m) (see *The Structure of Biological Membranes*, ed. by P. Yeagle, CRC Press, Boca Raton, Fla., 1991, in particular ch. 1-5, incorporated herein by reference.). Lipidic microparticles include, but are not limited to a liposome, a lipid-nucleic acid complex, a lipid-drug complex, a solid lipid particle, and a microemulsion droplet. Methods of making and using these types of lipidic microparticles and nanoparticles, as well as attachment of affinity moieties, e.g., antibodies, to them are known in the art (see, e.g., U.S. Pat. Nos. 5,077,057; 5,100,591; 5,616, 334; 6,406,713 (drug-lipid complexes); U.S. Pat. Nos. 5,576,016; 6,248,363; Bondi et al. (2003) *Drug Delivery* 10: 245-250; Pedersen et al. (2006) *Eur. J. Pharm. Biopharm.* 62: 155-162 (solid lipid particles); U.S. Pat. Nos. 5,534,502; 6,720,001; Shiokawa et al. (2005) *Clin. Cancer Res.* 11: 2018-2025 (microemulsions); U.S. Pat. No. 6,071,533 (lipid-nucleic acid complexes)).

A liposome is generally defined as a particle comprising one or more lipid bilayers enclosing an interior, typically an aqueous interior. Thus, a liposome is often a vesicle formed by a bilayer lipid membrane. There are many methods for the preparation of liposomes. Some of them are used to prepare small vesicles (d<0.05 micrometer), some for larger vesicles (d>0.05 micrometer). Some are used to prepare multilamellar vesicles, some for unilamellar ones. In certain embodiments for the present invention, unilamellar vesicles are preferred because a lytic event on the membrane means the lysis of the entire vesicle. However, multilamellar vesicles can also be used, perhaps with reduced efficiency. Methods for liposome preparation are exhaustively described in several review articles such as Szoka and Papahadjopoulos (1980) *Ann. Rev. Biophys. Bioengg.,* 9: 467; Deamer and Uster (1983) Pp. 27-51 In: *Liposomes,* ed. M. J. Ostro, Marcel Dekker, New York; and the like.

The nano-structured material whose cellular uptake is detected by the method according to any aspect of the present invention may have a structure selected from one of the following: hexagonal, cubic, tetragonal, rhombohedral, orthorhombic, monoclinic, triclinic and a combination thereof. In particular, the nano-structured material has a hexagonal lattice structure.

The nano-structured material whose cellular uptake is detected by the method according to any aspect of the present invention may comprise at least one dimension having size <1000 nm. For example, <100 nm, in particular, less than 50 nm. In particular, the nano-structured material comprises at least one dimension of size <25 nm. Even more in particular, the at least one dimension is of size <10 nm.

According to one aspect, the present invention provides a method of detecting uptake of a nano-structured material, wherein a biomolecule is attached to the nanostructured material. The biomolecule may be any suitable biomolecule. For example, the biomolecule is selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof.

The CMS methods of the invention can be used to measure not only the cellular uptake of metal nanoparticles but also the non-metal nano/micro particles. (J. A. Champion, S. Mitragotri, *Proc. Natl. Acad. Sci. U.S.A.* 2006, 103, 4930).

Nanometer-scale non-metallic drug carriers such as liposomes and polymersomes have been developed to deliver drugs to disease sites, and are increasingly common in clinical use. The principals of nanocarrier design and biological interactions are increasingly well understood, allowing tailored design of nanocarriers with specific drug delivery, targeting, and release characteristics.

The delivery of cytotoxic or chemotherapeutic agents to the site of a solid tumor is highly desired because systemic administration of these agents can result in killing not only the tumor cells, but also normal cells within the body. This toxicity to normal cells limits the dose of the cytotoxic agents and thus reduces their therapeutic potential.

CMS methods of the invention can be used to measure the quantity of nanocarriers, such as liposomes used for drug delivery (Y. Aoyama, et al., *J. Am. Chem. Soc.* 2003, 125, 3455; J. M. De la Fuente, et al., *Langmuir,* 2006, 22, 3286; A. Elbakry, et al., *Nano Lett.* 2009, 9, 2059) that are uptaken into cancer cells (T. Minko, et al., *Anti-Canc. Agents Med. Chem.* 2006, 6, 537).

Microparticles and nanoparticles, including liposomes, can have therapeutic agents (bioactive moieties) incorporated into their hydrophobic nanoparticle core in aqueous medium or organic solvents.

Bioactive agents (therapeutic agents) include, and are not limited to, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.). Bioactive agents may have been administered to an individual as disclosed herein. Exemplary therapeutic agents to be delivered in accordance with the present invention include, but are not limited to, small molecules (e.g. cytotoxic agents), nucleic acids (e.g., siRNA, RNAi, and mircoRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., prostate cancer).

Some examples of therapeutic agents that can be delivered within the nanoparticles produced in accordance with the disclosed methods include, but are not limited to agents such as penicillins, aminopenicillins, penicillins in conjunction with penicillinase inhibitor and/or anti-fungal agents), cephalosporins, cephamycins and carbapenems, fluoroquinolones, tetracyclines, macrolides and aminoglycosides. Specific examples include, but are not limited to, erythromycin, bacitracin zinc, polymyxin, polymyxin B sulfates, neomycin, gentamycin, tobramycin, gramicidin, ciprofloxacin, trimethoprim, ofloxacin, levofloxacin, gatifloxacin, moxifloxacin, norfloxacin, sodium sulfacetamide, chloramphenicol, tetracycline, azithromycin, clarithyromycin, trimethoprim sulfate and bacitracin.

Other examples of therapeutic agents suitable for inclusion within the disclosed nanoparticles are non-steroidal (NSAIDs) and steroidal anti-inflammatory agents (generally referred to as anti inflammatory agents (including both COX-I and COX-2 inhibitors)). Examples include, but are not limited to, corticosteroids, medrysone, prednisolone, prednisolone acetate, prednisolone sodium phosphate, fluormetholone, dexamethasone, dexamethasone sodium phosphate, betamethasone, fluoromethasone, antazoline, fluorometholone acetate, rimexolone, loteprednol etabonate, diclofenac (diclofenac sodium), ketorolac, ketorolac tromethamine, hydrocortisone, bromfenac, flurbiprofen, antazoline and xylometazoline.

Other therapeutic agents that can be incorporated into nanoparticles as disclosed herein include anti-histamines, mast cell stabilizers and other anti-allergy agents. Examples include, but are not limited, cromolyn sodium, lodoxamide tromethamine, olopatadine HCl, nedocromil sodium, ketotifen fumarate, levocabastine HCL, azelastine HCL, pemirolast (pemirolast potassium), epinastine HCL, naphazoline HCL, emedastine, antazoline, pheniramine, sodium cromoglycate, N-acetyl-aspartyl glutamic acid and amlexanox.

Other non-limiting examples of potentially suitable therapeutic agents for incorporation into nanoparticles include anti-cancer agents such as 5-fluorouracil (5-FU), CPT-I1, 10-hydroxy-7-ethylcamptothecin (SN38), S-I capecitabine, ftorafur, 5' deoxyfluorouridine, UFT, eniluracil, deoxycytidine, 5-azacytosine, 5-azadeoxycytosine, allopurinol, 2-chloroadenosine, aminopterin, methylene-10-deazaminopterin (MDAM), oxaplatin, picoplatin, tetraplatin, satraplatin, platinum-DACH, ormaplatin, CI-973, JM 216, and analogs thereof, 9-aminocamptothecin, 1 Ojl 1-methylenedioxycamptothecin, karenitecin, 9-nitrocamptothecin, TAS 103, L-phenylalanine mustard, ifosphamidemefosphamide, trophosphamide carmustine, epothilones A-E, tomudex, 6-mercaptopurine, 6-thioguanine, karenitecin, acyclovir, valacyclovir, ganciclovir, amantadine, rimantadine, lamivudine, zidovudine, bevacizumab, trastuzumab, rituximab, 20-epi-1, 25 dihydroxy vitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, antidorsalizdng morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-aminotriazole, carboxyamidotriazole, carest M3, carmustine, earn 700, cartilage derived inhibitor, carubicin hydrochloride, carzelesin, casein kinase inhibitors, castanospermine, cecropin B, cedefmgol, cetrorelix, chlorambucil, chlorins, chloroquinoxaline sulfonamide, cicaprost, cirolemycin, cisplatin, cisporphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, daclizimab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocanmycin SA, ebselen, ecomustine, edatrexate, edelfosine, edrecolomab, eflornithine, eflomithine hydrochloride, elemene, elsarnitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, ctoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, mopidamol, multiple drug resistance gene inhibitor, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein Abased immune modulator, protein kinase C inhibitor, protein tyrosine, phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone B1, ruboxyl, safmgol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride and combinations thereof.

In one embodiment, the nanoparticles of this invention can contain siRNA as a therapeutic agent. Preferably, the siRNA molecule has a length from about 10-50 or more nucleotides. More preferably, the siRNA molecule has a length from about 15-45 nucleotides. Even more preferably, the siRNA molecule has a length from about 19-40 nucleotides. Even more preferably, the siRNA molecule has a length of from about 21-23 nucleotides. The siRNA of the invention preferably mediates RNAi against a target mRNA. Commercially available design tools and kits, such as those available from Ambion, Inc. (Austin, Tex.), and the Whitehead Institute of Biomedical Research at MIT (Cambridge, Mass.) allow for the design and production of siRNA.

Cellular Uptake of Viral Nanoparticles

The CMS methods of the invention can be used to evaluate cellular uptake of viral nanoparticles. (J. Mercer, A. Helenius, *Science* 2008, 320, 531; A. Cooper, Y. Shaul, *J. Biol. Chem.* 2006, 281, 16563; G. Bao, X. R. Bao, *Proc. Natl. Acad. Sci. U.S.A.* 2005, 102(29):9997-8).

Endocytosis is used by eukaryotic cells to perform a wide range of functions, including the uptake of extracellular nutrients and the regulation of cell-surface receptors, as well as by toxins, viruses, and microorganisms to gain entry into cells. Endocytosis encompasses many different processes such as phagocytosis of large (>250 nm) particles. The understanding and quantitative analysis of the mechanisms underlying receptor-mediated endocytosis have important implications for not only viral pathogenesis but also the delivery of macromolecules and nanoparticles for intracellular imaging and targeted therapies. (Gao, H., Shi, W. & Freund, L. B. (2005) *Proc. Natl. Acad. Sci. USA* 102:9469-9474.)

While viral load, which is a measure of the number of virus particles present in the bloodstream, expressed as copies per milliliter is used in treatment decisions and to monitor the efficacy of a treatment, determination of the intracellular uptake of virus particles provides a more accurate assessment of the immune response as well as for the determination of therapeutic regimens. For example, herpesviruses routinely avoid effective immune response during infection by intracellular localization, as acutely observed in the case of Kaposi's Sarcoma associated gammaherpesvirus. (Adang L A, et al. *J. Virol.* 81(10):5079-5090 (2007).

Particles smaller than 100 nm are nanomaterials covering a range of sizes including that of human viruses such as Avian influenza and HIV. The average size of a HIV viral particle is about 100 nm, hepatitis C virus particles are about 35-40 nm. Airborne viral infection is commonly caused by inhalation of droplets of moisture containing virus particles. Larger virus-containing droplets are deposited in the nose, while smaller droplets or nano particles find their way into the human airways or alveoli. The SARS virus is spread by droplets produced by coughing and sneezing with the sizes around 100-500 nm (Donnelly et al. *Lancet*, 361, 1761-1777, (2003)). The present invention provides a means to detect and quantify a virus within a virus-infected mammalian cell, preferably the virus is selected from the group consisting of Influenza, Measles, Coronavirus, Mumps, Marburg, Ebola, Rubella, Rhinovirus, Poliovirus, Hepatitis A, Smallpox, Chicken-pox, Severe Acute Respiratory Syndrome virus or SARS virus (also referred to as SARS coronavirus), Human Immunodeficiency Virus (HIV) and associated nonhuman animal immunodeficiency retroviruses such as Simian Immunodeficiency Virus (SIV), Rotavirus, Norwalk virus and Adenovirus. Influenza viruses include both human and avian forms of the virus. In still another embodiment of the present invention, the viruses are selected from a group comprising helical viruses, icosahedral viruses, enveloped viruses and complex viruses.

In addition to measuring the severity of an infection more accurately, accurate measurement of intracellular virus particles (ICV) in an infected cell enables more specific measurement of the efficacy of anti-viral therapy. While ICV levels have been traditionally measured by detecting levels of a specific virus-associated particle (e.g., mRNA by Southern blot, or a viral protein by immunoassay), these procedures do not measure the levels of intact virus particles in the infected cell, and the results often overestimate ICV levels.

The CMS method of detection and quantitation of virus nanoparticles in the cell enable accurate measurements of intracellular virus particles (ICV). Phagocytosis is a principal component of the body's innate immunity in which macrophages and other antigen-presenting cells internalize large (>0.5 μm) particulate targets including those comprising viral and other pathogens, Measurement of intracellular uptake of inert (e.g., polystyrene) nanoparticles is an accepted model for measurement of efficacy of methods for determination of intracellular uptake of particles such as pathogens, including viruses. (Champion J A and Mitragotri S. *Proc Natl Acad Sci USA*. 2006 Mar. 28; 103(13): 4930-4934.)

In yet another embodiment of the present invention, the biological sample is selected from a group comprising infectious agents, disease causing agents, microorganisms. In still another embodiment of the present invention, the infectious agents are selected from a group comprising bacteria, viruses, fungi, protozoa and parasites.

In various embodiments, the methods measure uptake of a particle selected from the group consisting of a nanoparticle, a microparticle, a microcapsule, a cytotoxin, a drug, a liposome, and an antibody. In certain embodiments the particle comprises a moiety selected from the group consisting of a liposome, and a polymeric nanoparticle. In certain embodiments the particle comprises a liposome containing a moiety selected from the group consisting of an anti-cancer drug, a detectable label, and a radiosensitizing agent. In certain embodiments the particle comprises a lipidic microparticle or nanoparticle (e.g., a liposome, a lipid-nucleic acid complex, a lipid-drug complex, a solid lipid particle, a microemulsion droplet, etc.). In certain embodiments the microparticle or nanoparticle comprises a pharmaceutical. In certain embodiments the microparticle or nanoparticle is a liposome (e.g., a multilamellar liposome or a unilamellar liposome). The liposome can, optionally, be a stearically stabilized liposome. In certain embodiments the liposome or other lipidic particle contains an anti-cancer pharmaceutical or an anti-cancer siRNA, or another active agent.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

CMS Instrumentation and Sample Preparation

The experimental setup of CMS comprised a laser-induced acoustic desorption of microparticles without a matrix, a low-frequency quadrupole ion trap for ultra-large m/z measurement, a pressure controlled corona discharge to enhance the number of charges on a cell or microparticle, and a compact and low-noise charge detector for total-charge measurement. A frequency-doubled Nd:YAG laser beam ($\lambda$=532 nm, Laser Technik, Berlin, Germany) with a pulse duration of approximately 6 ns was shined directly onto the backside of the sample plate to desorb cells by laser-induced acoustic desorption (LIAD) with a power density of around $10^8$ W/cm$^2$. Laser energy at 30 mJ/pulse was used to irradiate the sample from the back side of the wafer. The RF voltage was set at ~3000 Vp-p. The microparticles from the laser desorption were trapped with an ac field (ca. 350 Hz-20 Hz, 5 sec) in a helium buffer gas (ca. 65 mTorr). To prepare the sample for LIAD, an aliquot (10 µL) of the purified particle suspension (containing ~1×10$^2$ particles/mL) was deposited onto an ~400 µm thick Si wafer and dried under a desiccated box.

Example 2

Cell Culture

Mouse leukemic monocyte macrophage cell line Raw 264.7, human embryonic carcinoma cell line NTERA2, and human cervical cancer cell line HeLa were obtained from American Type Culture Collection (ATCC) and cultured with minor modifications according to their specifications. Briefly, cells were cultured at 37° C. under a 5% $CO_2$ atmosphere in Dulbecco's Modified Eagle's Medium (DMEM) or RPMI 1640 medium containing 10% fetal calf serum (FCS), 2 mM L-Glutamine, and 1% standard penicillin/streptomycin (10,000 IU/ml) (all from Life Technologies, Carlsbad, Calif.). In our experiments, HeLa, Raw264.7, and NTERA2 cells were incubated with gold nanoparticles or polystyrene particles with various sizes for indicated times in completed medium. After the allotted time, the cells were detached from the Petri dish surface using the enzyme trypsin, homogenized the cells, and then washed with Dulbecco's phosphate-buffered saline (PBS, Gibco BRL) and fixed with 4% paraformaldehyde in PBS for 15 minutes at room temperature. Thereafter, the cells were washed three times in distilled de-ionized water and were subsequently counted via Vi-CELL series Cell Viability Analyzer (Beckman Coulter, USA) to determine the total cell number and re-suspended before they were placed into mass spectrometer or ICP-MS for analysis.

Example 3

ICP-MS Instrumentation

An X series II ICP-MS (Thermo-Electron, Winsford, Cheshire, UK) was used for the determination of gold concentration. A microwave (MARSXpress, CEM Corporation, U.S.A.) digestion equipped with temperature and a pressure sensor was used for cell samples digestion using vessels.

Example 4

ICP-MS Sample Preparation and Measurement

All the polypropylene containers were soaked in 7% v/v nitric acid $HNO_3$ (Ultrex II, J. T. Baker Inc., Phillipsburg, N.J.) for 24 h and cleaned with deionized water. Accurately weighted 200 mL cell samples were transferred into pre-cleaned high pressure vessels, to which 2 mL aqua regia was added. These vessels were closed and heated in a microwave cavity using optimized microwave program for heating them for 15 min until 190° C. at 200 W and step 2 maintaining 10 min at 190° C. at 200 W. These vessels were cooled to room temperature. These solutions were made up to 50 mL using deionized water, without using any drying step. Cellular uptake experiments with each gold nanoparticles (AuNPs) were repeated 3 times, and each replicate was measured 7 times by ICP-MS. Calibration standard solution (1000 mg/L, Gold ICP standard, Merck, Darmstadt, Germany) was diluted with deionized water (50 ppb, 25 ppb, 10 ppb, 5 ppb, 1 ppb). Each standard solution was measured by ICP-MS and did the linear regression till c=0.9999. The resulting calibration line was used to determine the gold amounts taken up by the cells in each sample. A 7% solution of nitric acid was used to wash the instrument between analyses to facilitate gold removal.

Example 4

Quantitation of Cellular Uptake of Lentivirus

The human leukemic cell line CEM were incubated with lentiviruses at MOI=3 for the indicated times in complete medium containing 8 ng/ml of polybrene. After the allotted time, the cells were washed with a cold Dulbecco PBS (Gibco BRL) to remove free viruses and fixed with 4% paraformadehyde in PBS for 15 minutes at room temperature. The cells were then washed three times in distilled deionized water and were counted by using a Vi-CELL series cell-viability analyzer (Beckman Coulter, USA) to determine the cell number. The cells were resuspended before they were placed in the cell mass spectrometer for analysis.

Figure 7:
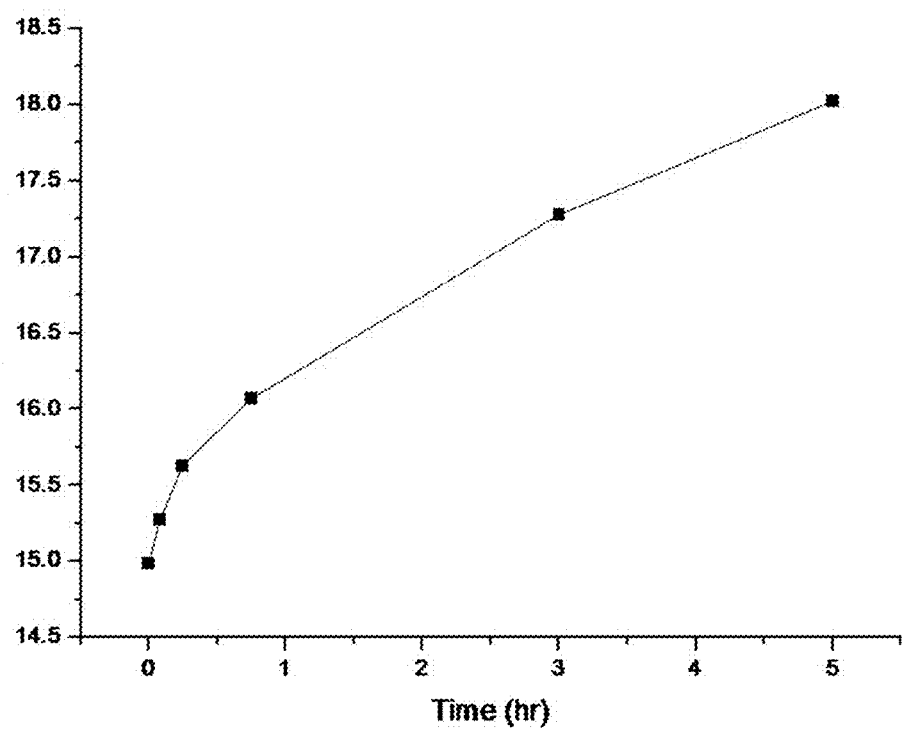
FIG. 7 shows the mass of human CEM cell line over a 5 hour time period, following infection with lentivirus at MOI=3 as determined by cell mass spectrometry.

At 5 hr post-infection, the increase in mass of the infected cells (mass difference) is about $3.0 \times 10^{13}$ Da as shown in FIG. 7. The molecular weight of each lentivirus is $3.55 \times 10^8$ Da, therefore about 84,500 viruses were taken up by each CEM cell on average.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. A method for quantifying a number of nanoparticles taken up by an individual cell, the method comprising the steps of:
   (a) contacting a cell with a nanoparticle of dimension less than 1 µm, under conditions suitable for uptake of the nanoparticle by the cell, and incubating for a specific period of time;
   (b) recording a mass spectrum of the cell by cell mass spectrometry, wherein the process of cell mass spectrometry comprises:
   mounting and desorbing/vaporizing the cell into a gas phase;
   enhancing the number of charges on the cell;
   measuring a mass to charge (m/z) ratio by a mass analyzer; and
   measuring the total number of charges (z) on the cell by a charge detector coupled to the mass analyzer;
   (c) measuring a mass/charge (m/z) ratio of the cell contacted with the nanoparticle and a mass/charge (m/z) ratio of a corresponding cell not contacted with the nanoparticle;
   (d) measuring an absolute mass of each cell with an uptake of nanoparticles from the acquired values of m/z and the corresponding charge (z) on the cell, wherein the cell with an uptake of the nanoparticles shows an upward shift in m/z ratio; and
   (e) measuring the number of nanoparticles taken up by the individual cell within the specific period of time from a mean mass difference, wherein a mass difference corresponding to a known number of the nanoparticle of a known dimension is predetermined as a standard.

2. The method of claim 1, further comprising:
   detecting charges carried on each cell by a Faraday plate charge detector.

3. The method of claim 1, wherein the m/z ratio of the cell is within a range of $10^9$ to $10^{10}$.

4. The method of claim 1, further comprising:
   measuring mass to charge (m/z) ratio and the total number of charges (z) on the cell in contact with the nanoparticles over time; and
   producing a time-resolved uptake profile of the nanoparticle by the cell.

5. The method of claim 1, wherein the nanoparticle has a dimension less than or about 500 nm, less than or about 250 nm, less than or about 100 nm, less than or about 50 nm, less than or about 30 nm, less than or about 20 nm, less than or about 10 nm, or less than or about 5 nm.

6. The method of claim 1, wherein the nanoparticle is metallic.

7. The method of claim 6, wherein, the nanoparticle is selected from gold, silver or palladium.

8. The method of claim 1, wherein the nanoparticle or microparticle is non-metallic.

9. The method of claim 8, wherein the nanoparticle or microparticle is a polystyrene nanoparticle.

10. The method of claim 8, wherein the nanoparticle comprises polymeric nanoparticles (NPs), liposomes, viral-based NPs, carbon nanotubes, diamond NPs, and polymeric micelles, a nanocarrier, a liposome, a drug nanoparticle, or viral nanoparticles.

11. The method of claim 8, wherein the nanoparticle comprises a lipidic particle.

12. The method of claim 9, wherein the lipidic particle is selected from a a liposome, a lipidnucleic acid complex, a lipid-drug complex, a solid lipid particle, and a microemulsion droplet.

13. The method of claim 8, wherein the nanoparticle comprises a structure selected from one of the following: hexagonal, cubic, tetragonal, rhombohedral, orthorhombic, monoclinic, triclinic and a combination thereof.

14. The method of claim 8, wherein the nanoparticle comprises a suitable biomolecule attached to a nanocarrier particle.

15. The method of claim 14, wherein the biomolecule is selected from the group consisting of: protein, nucleic acid, nucleosides, nucleotides, DNA, hormone, amino acid, peptide, peptidomimetic, RNA, lipid, albumin, antibody, phospholipids, glycolipid, sterol, vitamins, neurotransmitter, carbohydrate, sugar, disaccharide, monosaccharide, oligopeptide, polypeptide, oligosaccharide, polysaccharide and a mixture thereof.

16. The method of claim 1, wherein the nanoparticles have therapeutic agents or bioactive moieties incorporated into their hydrophobic core.

17. The method of claim 16, wherein the bioactive moiety is selected from the group consisting of diagnostic agents, contrast agents, radionuclides, fluorescent, luminescent, and magnetic moieties, prophylactic agents, vaccines, and nutraceutical agents.

18. The method of claim 16, wherein the therapeutic agent is selected from the group consisting of small molecules, nucleic acids, siRNA, RNAi, microRNA, proteins, antibodies, peptides, lipids, carbohydrates, hormones, metals, radioactive compounds, drugs, vaccines, immunological agents and combinations thereof.

19. The method according to claim 1, wherein the cell mass spectrometry is selected from a charge monitoring cell mass spectrometry (CMCMS), and a mass spectrometer with trapping capability with light scattering detection.

20. The method of claim 19, wherein the mass spectrometer with trapping capability is an ion trap mass spectrometer or Fourier transform Ion Cyclotron Resonance (FTICR) mass spectrometer.

* * * * *